(12) United States Patent
Carew

(10) Patent No.: US 10,981,085 B2
(45) Date of Patent: Apr. 20, 2021

(54) CONTINUOUS EXTRACTION OF NATURAL PRODUCTS FROM PLANTS APPARATUS AND METHODS

(71) Applicant: E. Bayne Carew, Naples, FL (US)

(72) Inventor: E. Bayne Carew, Naples, FL (US)

( * ) Notice: Subject to any disclaimer, the term of this patent is extended or adjusted under 35 U.S.C. 154(b) by 0 days.

(21) Appl. No.: 16/744,894

(22) Filed: Jan. 16, 2020

(65) Prior Publication Data
US 2020/0222830 A1    Jul. 16, 2020

Related U.S. Application Data

(63) Continuation-in-part of application No. 16/598,682, filed on Oct. 10, 2019, and a continuation-in-part of
(Continued)

(51) Int. Cl.
*B01D 11/02* (2006.01)
*B01D 29/35* (2006.01)
(Continued)

(52) U.S. Cl.
CPC ...... *B01D 11/0288* (2013.01); *B01D 11/0296* (2013.01); *B01D 29/35* (2013.01);
(Continued)

(58) Field of Classification Search
CPC ............ B01D 11/0284; B01D 11/0288; B01D 11/0296; B01D 61/246; B01D 29/35; B01D 29/66; B01D 2011/005; B01D 2011/002; B01D 11/0226; C07C 37/685; C07D 311/80; C07D 311/72
See application file for complete search history.

(56) References Cited

U.S. PATENT DOCUMENTS 6,596,172 B1 *   7/2003   Kopf .................... B01D 15/361
                                                                210/198.2
10,245,525 B1 *   4/2019   Ko ........................ B01D 11/02
(Continued)

OTHER PUBLICATIONS

Kitryte et al, Food Chemistry 267 (2018) 420-429.*
Zhang et al China Med (2018) 13:20.*

*Primary Examiner* — Krishnan S Menon
(74) *Attorney, Agent, or Firm* — Gregory D. DeGrazia; Miller, Canfield, Paddock & Stone PLC

(57) ABSTRACT

A reaction assembly separating plant material from water includes a first annular filter element defining an axis. The first annular filter element is defined by an outer annular coil of flat wire and an optional second filter element is defined by an inner annular coil of flat wire, being generally helical in the axial direction. A cylindrically or frustoconical filter membrane is concentrically disposed between the first and second annular filter element. The filter membrane is porous having aperture size of less than a nano-particulate size of the plant material, but greater than a nano-particulate size of the water molecule. The second annular filter includes adjustable porosity for selectively preventing particles from reaching the filter membrane and selectively cleaning the membrane by reversed flow of water through the membrane. The assembly generates radial and distal flows and differential pressure forces, for use in high throughput industrial, agricultural and municipal facilities.

13 Claims, 8 Drawing Sheets

Related U.S. Application Data application No. 16/548,457, filed on Aug. 22, 2019, now Pat. No. 10,583,396.

(60) Provisional application No. 62/798,723, filed on Jan. 30, 2019, provisional application No. 62/793,043, filed on Jan. 16, 2019.

(51) Int. Cl.
| | | |
|---|---|---|
| *C07C 37/68* | (2006.01) | |
| *C07D 311/80* | (2006.01) | |
| *C07D 311/72* | (2006.01) | |
| *B01D 29/66* | (2006.01) | |
| *B01D 61/24* | (2006.01) | |
| *B01D 11/00* | (2006.01) | |

(52) U.S. Cl.
CPC .......... *B01D 29/66* (2013.01); *B01D 61/246* (2013.01); *C07C 37/685* (2013.01); *C07D 311/72* (2013.01); *C07D 311/80* (2013.01); *B01D 2011/002* (2013.01); *B01D 2011/005* (2013.01)

(56) References Cited

U.S. PATENT DOCUMENTS

| 2002/0134704 A1* | 9/2002 | Mitchell | B01D 11/0203 208/13 |
| 2009/0001027 A1* | 1/2009 | Carew | A01K 63/045 210/748.13 |
| 2017/0333505 A1* | 11/2017 | Gharib | A61K 31/192 |

* cited by examiner

CONTINUOUS EXTRACTION OF NATURAL PRODUCTS FROM PLANTS APPARATUS AND METHODS

PRIOR APPLICATIONS

The present application claims priority as a Continuation-In-Part application to U.S. patent application Ser. No. 16/598,682 as a Continuation-In Part application that claims priority to U.S. patent application Ser. No. 16/548,457 filed on Aug. 22, 2019 that claims priority to U.S. Provisional Patent Application No. 62/785,405 filed on Dec. 27, 2018 and to U.S. Provisional Patent Application No. 62/793,043 filed on Jan. 16, 2019 and to U.S. Provisional Patent Application No. 62/798,723 filed on Jan. 30, 2019, the contents each of which are incorporated herein by reference.

TECHNICAL FIELD

The present invention relates generally toward a continuous plant product extraction reactor apparatus and method. More specifically, the present invention relates to a plant product extraction reactor apparatus and method that behaves as a membrane separating internal solid reactants from generally external solvent-hydrodistillate fluid products thereby stripping valuable organic content from solid plant structures.

BACKGROUND

Co-pending U.S. patent application Ser. Nos. 16/598,682 and 16/548,457 disclose a unique filtration system used for drying sludges and desalination, respectively while producing clean water, the contents each of which are incorporated herein by reference. However, it is believe that further modifications of these devises may be beneficial in the extraction of natural constituents from plants such as, for example terpenes, or more generally, secondary metabolites. Terpenes represent a diverse class of isoprenoid based structures, one of which includes cannabinoids referred to herein. These are derived mainly from tissues of terrestrial plants. However, other plants provide other useful terpenes or terpenoids including, for example, essential oils, perfumery, flavoring and some vitamin extracts. Efficient extraction of these natural products has proven elusive due, in part, to the requirement of batch extraction and the inability to provide continuous processes.

These natural products are valued for pharmaceutical and nutraceutical properties, with market sizes in the $10-20 billion range. Usually, these accessory products individually are in the 1% or less of the plant; their extraction is expensive and with few exceptions due batch processes. In addition, cannabinoids and related terpenes appear to provide a significant source of emerging pharmaceutical and medical uses. In addition, the rapid growth in interest of cannabinoids has spawned a renewed interest in natural, plant based products. Reducing the cost by automation and in continuous processing, as the invention of the present application demonstrates, has proven elusive.

Therefore, there exists a need for an improved method of extracting natural plant based products that will enhance the research and development into natural medicaments and the like.

SUMMARY

A method and system for extracting constituents from plant material is disclosed. A first and a second reactor assembly are provided. Each reactor assembly includes a first annular filter element defined by an outer annular coil of a flat wire providing adjustable filtration apertures. The first annular filter element defines a reaction side being disposed radially inwardly of the outer annular coil and a filtrate chamber 27 being disposed radially outwardly of the outer annular coil. A stream of plant solids including a first constituent and a second constituent is delivered into the reaction side of the first reactor assembly. First extracting fluids are disposed at a first temperature and composition and are injected into the reaction side of the first reactor assembly for solubilizing the first constituent of the plant solids. The first constituent is separated from the plant solids through the first annular filter element into the filtrate chamber 27 of the first reactor assembly.

A residuum of the plant solids disposed in the reaction side of the first reactor assembly is transferred to the reaction side of the second reactor assembly. Second extracting fluids are injected into the reaction side of the second reactor assembly along with the residuum. The second extracting fluids are disposed at a second temperature and composition for solubilizing the second constituent of the plant solids. The second constituent is separated from the second constituent through a second annular filter element into the filtrate chamber 27 of the second reactor assembly.

The system of the present invention relates to seriatim of filtration devices, automated and self-cleaning used for extracting natural products from plant tissue. The filtration elements may or may not be aperture adjustable. A screw conveyor is disposed within the reaction side of each filter element with including spiral fins and a central porous shaft through which the extraction fluids are injected into the reaction side of the filtration element at in a high pressure stream. In one embodiment, the extraction fluids include a mixture of alcohol and water. Alternatively, oleophilic solvents, with our without water are injected into the reaction side of the filter element in a high pressure steam. The extraction fluid being disposed in this phase is believed to denature the proteins to which the valuable oils are bound and break open the plant's cellular structure. In one embodiment, the stream of extracting fluids will include a third oil phase when the stream is superheated to a temperature corresponding to a vapor pressure point of the desired oily first constituent resulting in an oil-solvent-steam exiting the reaction side of the filter element through aperture defined by the annular coil. The filtrate chamber 27 of the reactor assembly receives the oil-solvent-stream in which the stream is cooled by way of a cooling element. Thus, the filtrate chamber 27 of the reactor assembly acts as a cooling a collection vessel for the constituent that is extracted from the plant solids.

This three-phase mixture that makes up the filtrate of the plant solids is thus hydro distilled into the chamber surrounding the filter element. The screw conveyor conveys the plant solids, following extraction of the constituent, toward a distal end of the reactor chamber. The fate of these remaining plant solids that make up the residuum depends on whether all of the desired natural constituents have been completely extracted from the solid phase. Completion is determined by monitoring the output of the oil-solvent at a temperature just below the vapor point of the solvent. The remaining water/steam is thereafter condensed below its boiling point. Each filter element may consist of a single helical coil as disclosed in U.S. Pat. Nos. 6,761,270 and 7,122,173, the contents of which are incorporated herein by reference. Alternatively, the each filter element may include inner and outer helical coils with a filter membrane disposed there between as disclosed in co-pending U.S. patent application Ser. Nos. 16/598,682 and 16/548,457, the contents of which are incorporated herein by reference.

A series of first and second reactor assemblies may be combined in sequence through a flange coupling for sequential extraction at temperatures and extraction fluid composition determined most useful for various constituent extraction. The plant oils and accessory flavonoid making up each constituent have distinctive boiling temperatures, generally ranging between about 200° F. and 365° F., for which reason first and second (or more) reaction chambers may be connected in sequence to perform extractions at molecularly characteristic hydrodistillation temperatures. As noted above, the filter elements making up the filtration media consists of apertures which are adjustable, that are responsive to automated self-cleaning demand cycles, when necessary. This filtration media, enclosing the screw conveyor type blades, need only have limited wall thickness, while the filter apertures are easily opened and closed to preset levels, by automated piston or screw means. As noted, the inventive reaction assemblies of this invention are described, in one embodiment for dewatering, but also may be combined in sequence for the purposes of hydrodistillation at progressive temperatures as is one embodiment of this application. The description the hydrodistillation embodiments are illustrated to accomplish sequential constituent extraction, which are adaptable to several natural product streams of different composition or through-put requirements.

As explained further herein below, the assembly 10 may be arranged as a dual or multiple assemblies 10 arranged in series for extracting valuable products from plants. By way of example, cannabinoid's harvested from three plant species known to produce cannabidiol compounds are known to include beneficial constituents and byproducts. These are often represented and abbreviated as THC, CBD, CBN, CBC, together with terpenoids and flavonoids, each of which (with the exclusion of THC) is known to possess useful medicinal properties. The serial assembly as represented in FIG. 8 is designed to separate these products based on solubility and boiling point in a vaporized solution of solvent and water, in this cannabinoid extraction example, 50/50 mixture of ethanol and water. However, other solvent and water mixtures are also within the scope of this invention and are selected to accommodate extraction of preferential constituents.

The plant solids enter the chamber uniformly radial out of a hollow drive shaft that drives the fins of the conveyor screw and are extracted from center radially outwardly with, in one embodiment, a travel radius of generally 3 inches for outputs of approximately 7 pounds per minute would and a conveyor screw running at 30 rpm. In radial, internal shaft entry of this embodiment, the water filtrate is instantly mobile, passing into the output, subject (as in flash processing) to both vacuum externally of the filter element and pressure internally of the filter element. Should the filter element become blocked with fine and adhesive solids, there is programmed a self-cleaning backwash, where the backwash may utilize product water and/or solvents, or steam and even the constituent as may be necessary.

The loading time and backwash is regulated by a central processing unit (CPU), programmed to configure CPU hardware, assembly relays, pumps, valves and accessories. The flexible CPU, includes external digital controls to manage the heat extraction process and corresponding backwash media loading rate. It will be noted that the external enclosing chamber and internal mechanisms are not restricted to cylindrical or conical shapes or internal mechanisms, but will generally include solids transport means. It will be apparent from the illustrations that the aperture of the filter element opening and closing mechanism is also enabled by a compressive piston to force the freed water radially out the enclosing filter into filtrate chamber 27 of the reactor assembly, which is emptied under partial vacuum.

In particular, the invention of the present application is automated and self-cleaning while providing the benefit of both dewatering and deodorizing both municipal and industrial plant material sludge. The dewatering assembly provides for adjustable filtration apertures and includes screw conveyor type fins that are interconnected to a porous rotating shaft into which compressed dry air may also be delivered. The dry air may also be augmented with oxidizing agents that deodorize, sterilize and dehydrate the organic sludge. The oxidizing agents are selected to assist stripping bound water from the organic matter.

In one embodiment, heat and augmented flues enter the inlet waste stream uniformly radially from a center outward having a travel radius of three inches for outputs approximately seven pounds per minute, which optimally includes the conveyor shaft rotating at about thirty rotations per minute with partially dried solids and enhanced speeds when processing watery suspensions. If this were a conventional dewatering assembly, the water extraction rate would depend on longitudinal diffusion (as with settling ponds) with media resistance determining the water extraction rate. In radial (internal) entry employed herein, the water filtrate is instantly mobile, passing into the filtrate side, subject (as in flash processing) to both vacuum externally to the filtrate chamber of the dewatering assembly and pressure internally to the sludge side of the dewatering assembly. Should the filtration media become blocked with fine and adhesive solids, there is programmed a self-cleaning backwash, where the backwash may utilize product water and/or waters or steam as may be necessary that will be described further herein below.

BRIEF DESCRIPTION OF THE FIGURES

Other advantages of the present invention will be readily appreciated, as the same becomes better understood by reference to the following detailed description when considered in connection with the accompanying drawings, wherein.

DETAILED DESCRIPTION

Figure 1:
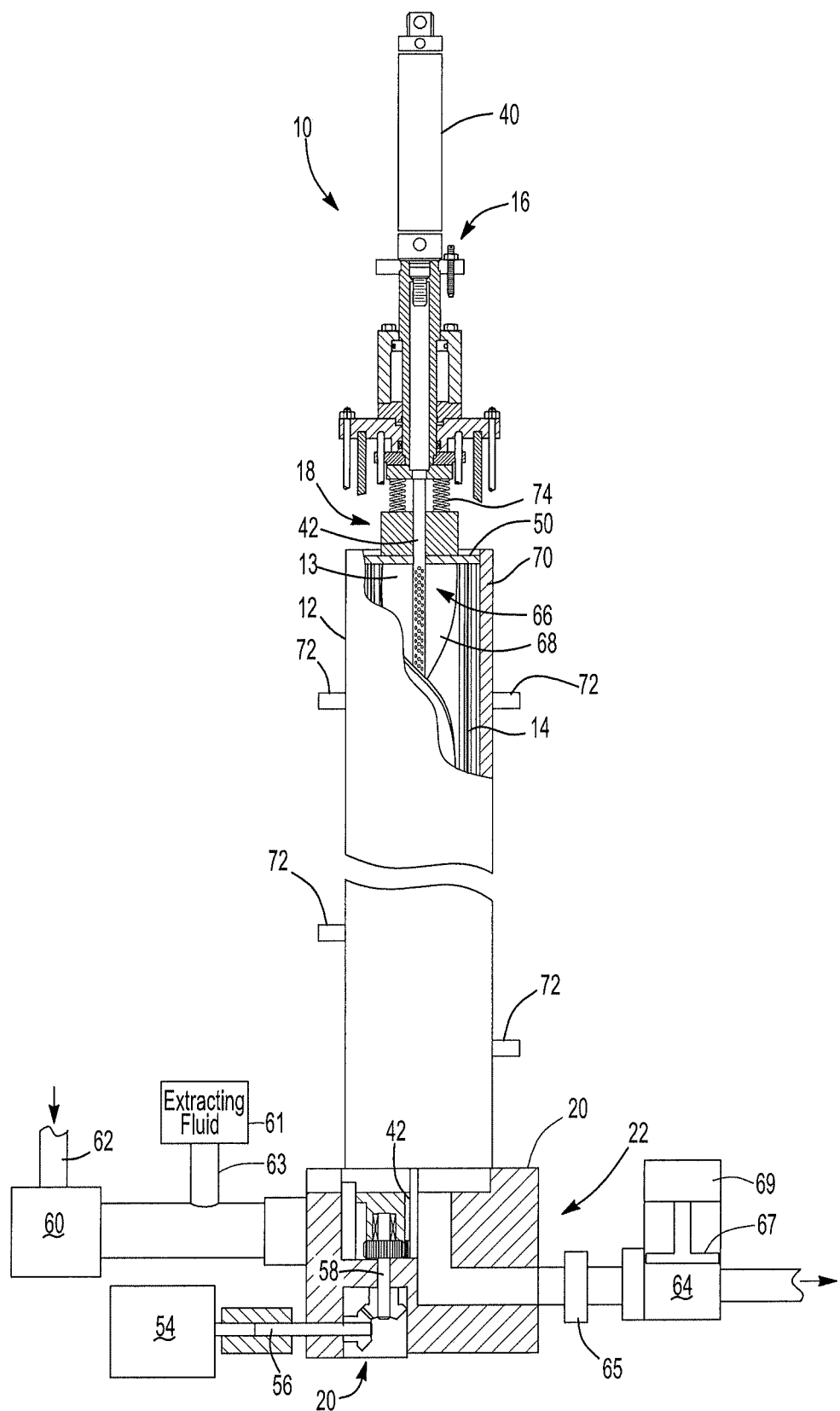
FIG. 1 shows a side schematic view of reactor assembly of the present invention.

Referring to FIG. 1, a side view of one embodiment of a reaction assembly of the present invention is generally shown at 10. A housing 12 encloses a variable aperture filter apparatus 14, the function of which will become more evident herein below. While variable apertures filtration is included within the scope of this application, it should be understood by those of ordinary skill in the art that filtration exclusive of variable apertures is also within the scope of this invention. An aperture drive mechanism 16 is disposed upon a first end 18 of the reaction assembly 10 and plant feed control assembly 20 is disposed upon a second end 22 of the reaction assembly 10.

Figure 2:
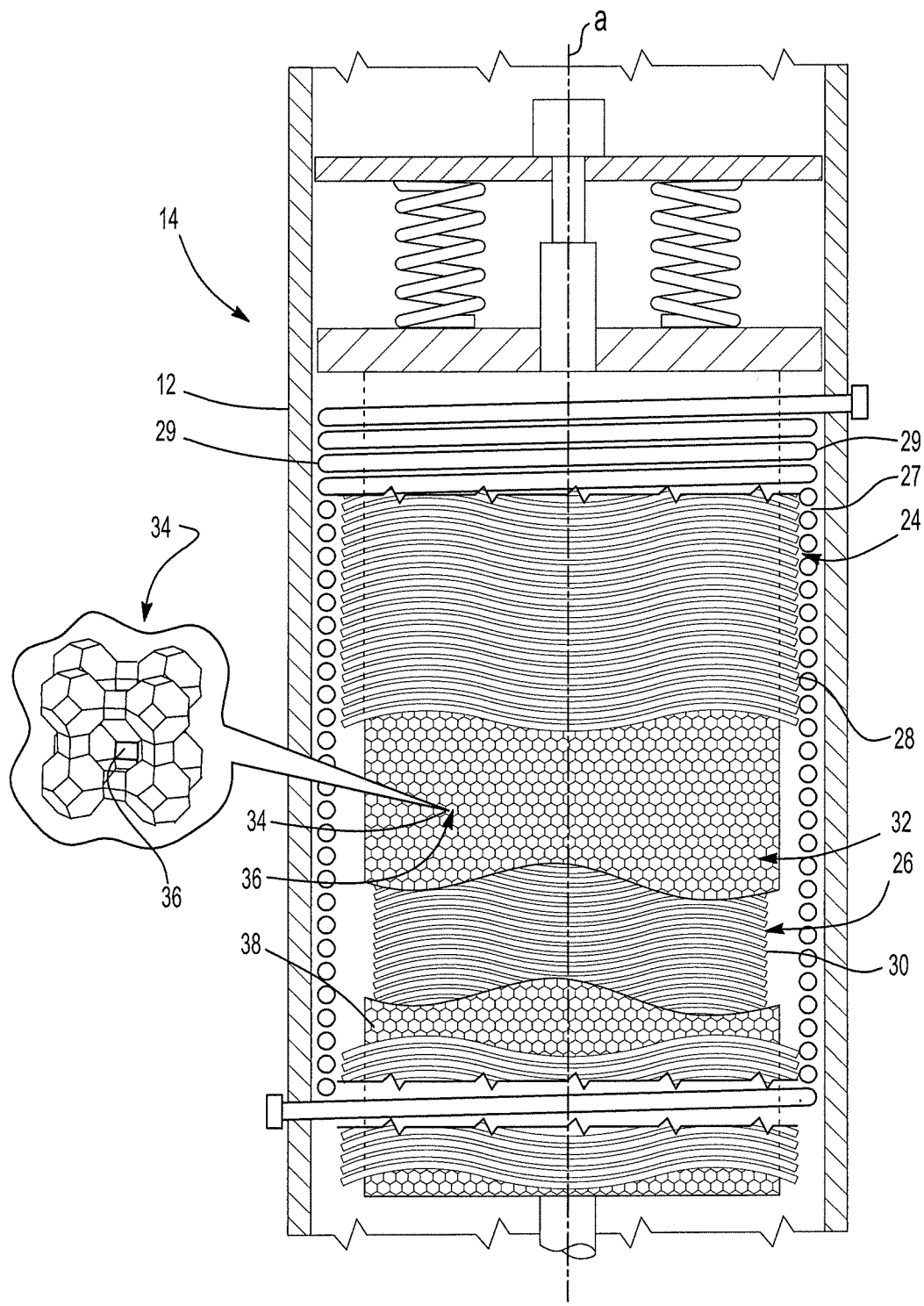
FIG. 2 shows a partial view of the inner and outer annular filter elements concentrically enclosing a filter membrane.

Referring now to FIG. 2, wherein a schematic of the filter apparatus 14 is shown including an inner annular filter element 24 and an outer annular filter element 26 that defines an inner reaction chamber 13 (FIG. 1). In one embodiment, only the inner annular filter element 26 is implemented. However, the outer annular filter element 26 is included to provide additional filtration, and even further purification at a molecular level when included with additional filtration media as will be explained further herein below. The outer annular filter element 24 is disposed radially outwardly of the inner annular filter element 26, when included. The outer annular filter element 24 is formed from an outer annular coil 28 of flat wire being generally helical in an axial direction and the inner annular filter element 26 is formed from an inner annular coil 30 of flat wire that is also generally helical in the axial direction. Because the inner annular filter element 26 is received concentrically inwardly of the outer annular filter element 24, a diameter of the inner annular filter element 26 is less than a diameter of the outer annular filter element 24. The configuration of the outer annular filter element 24 and the inner annular filter element 26 are both substantially the same as the wave coil disclosed in U.S. Pat. No. 6,761,270 WAVE COIL REACTION ASSEMBLY, and U.S. Pat. No. 7,122,123 METHOD OF FILTERING A FLUID WITH A REACTION ASSEMBLY the contents both of which are included herein by reference. Therefore, it should be understood by those of skill in the art that a size of apertures disposed between sequential coils (porosity) of the flat wire are adjustable by way of adjusting compression on the annular filter elements, the purpose of which will be described further herein below.

Each of the outer annular coil 24 and the inner annular coil 26 are formed from a single helical coil of flat wire stock providing adjacent coil gaps of between 2 microns and 20 microns when closed for filtration and about 250 microns when open for backwash and cleaning. Crimped spring steel from sources such as, for example IndiaMART and Smalley Steel suffice depending on price point. In one embodiment, Smalley Steel may provide three inch height stacked segments by ten to twelve inch diameter segments. Segmented assembly may be of particular use due to the formation of a filter membrane 32 that is embedded between the outer annular filter element 24 and the inner annular filter element 26. Such annular wave spring segments may be capped with flat retainer rings or shims, such that the first and second filter elements may be more readily assembled with the enclosed zeolite and/or graphene membranes as subunits noted in this embodiment. So also the similarly conical or frustoconical alternative illustrated in FIG. 7, where radial and tangential gravitational forces are enabled.

In another embodiment of the Inventor's disclosed wave coil 28, 30, as in the United States Patents incorporated by referenced above, the nano-apertures may be generated between the coil's opposed flat surfaces. When the wave coils' 28, 30 apertures are reduced to zero by compression, the flat opposing surfaces may be pre-formed to contain laser etched nano-pore grooves. These would have widths at least 0.050 microns and densities of 100 grooves per millimeter, radially disposed on the surfaces of the filters' flat wire. The purpose of such mesoporous grooved surface in the first 24 annular elements is to channel constituents as may penetrate the incompletely closed apertures of the filter elements 24, 26. More complex constituents may require filtration layering, such as anticipated of for saline or brackish or bio-waste fluids. Under high pressures the disorganized constituents may aggregate or condense into molecular level sheets, external to the membrane enclosed between the inner and outer filter elements 26, 24. Physical chemistry confirms the formation of such condensed sheets, which will flow parallel to the membrane 32; during backwash, these sheets are broken up into fibrils, passing in reverse direction back through the mesoporous containing filter 24 and into the residuum discharge outlet 65.

Figure 7:
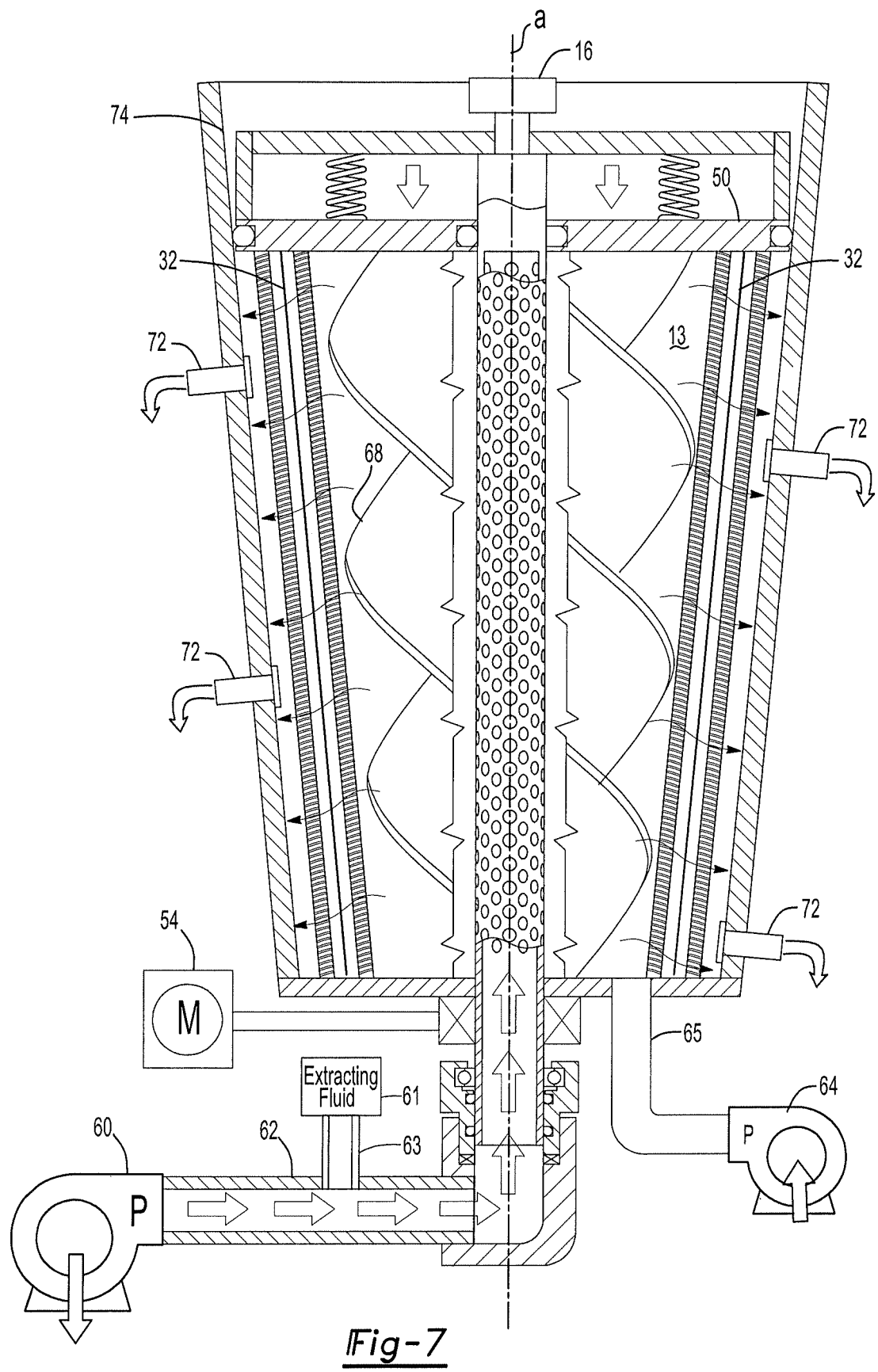
FIG. 7 shows an alternative conical shaped assembly.

The filter membrane 32, in one embodiment, includes a tubular shape, or alternatively, in another embodiment a frustoconical shape as is represented in FIG. 7, and is disposed between the outer annular filter element 24 and the inner annular filter element 26 so that the outer annular filter element 24 is disposed radially outwardly of the filter membrane 32 and the inner annular filter element 26 is disposed radially inwardly of the filter membrane 32 presenting concentric alignment in the axial direction so that a common axis is defined. The filter membrane 32 is formed to define molecular sized membrane pores 36 for entrapping plant material or solid plant products while allowing water, solvent, and oily constituents disposed in with the separate plant solids to pass through. In one embodiment, the filter membrane 32 is formed from zeolite 34, which is deposited on a carrier membrane 38. The zeolite includes zeolite pores 36 having porosities generally less than 5 nanometers are formed in a slurry, where such media is laser 3D printed on the surface of the carrier filter as membrane 32 on the surface of carrier membrane 38. The carrier membrane 36 in some applications has a thickness in the order of 0.1 to 0.5 microns, where the membrane's 36 maximum thickness ideally will be kept to no greater than 0.05 microns. At such thicknesses, the zeolite slurry is 3D printed and laser sintered circumferentially and radially to form the filter membrane 32. When enclosed within the inner and outer filter elements 26, 24, the formed membrane will resist differential fluid pressures external to the membrane and vacuum externally during filtration. The membrane 32, thus supported between the outer annular filter element 24 and the inner annular filter element 26 enables maximum constituent transport with sufficient stability, even as a monolayer. It should be understood that dewatering, drying the organic materials and transport of oily constituent is achievable as described with or without the membrane. However, with the membrane to achieve both solid slurry (~95% water or fluid) drying, water purification and transport of oily constituents, the pressure differential across the membrane is believed to be of 4 or 5 orders of magnitude difference. It should therefore be understood that the assembly 10 may be configured in a plurality of different combinations, including, but not limited to serial combinations, to meet specific needs of a particular purpose as will be explained further herein below.

Figure 3:
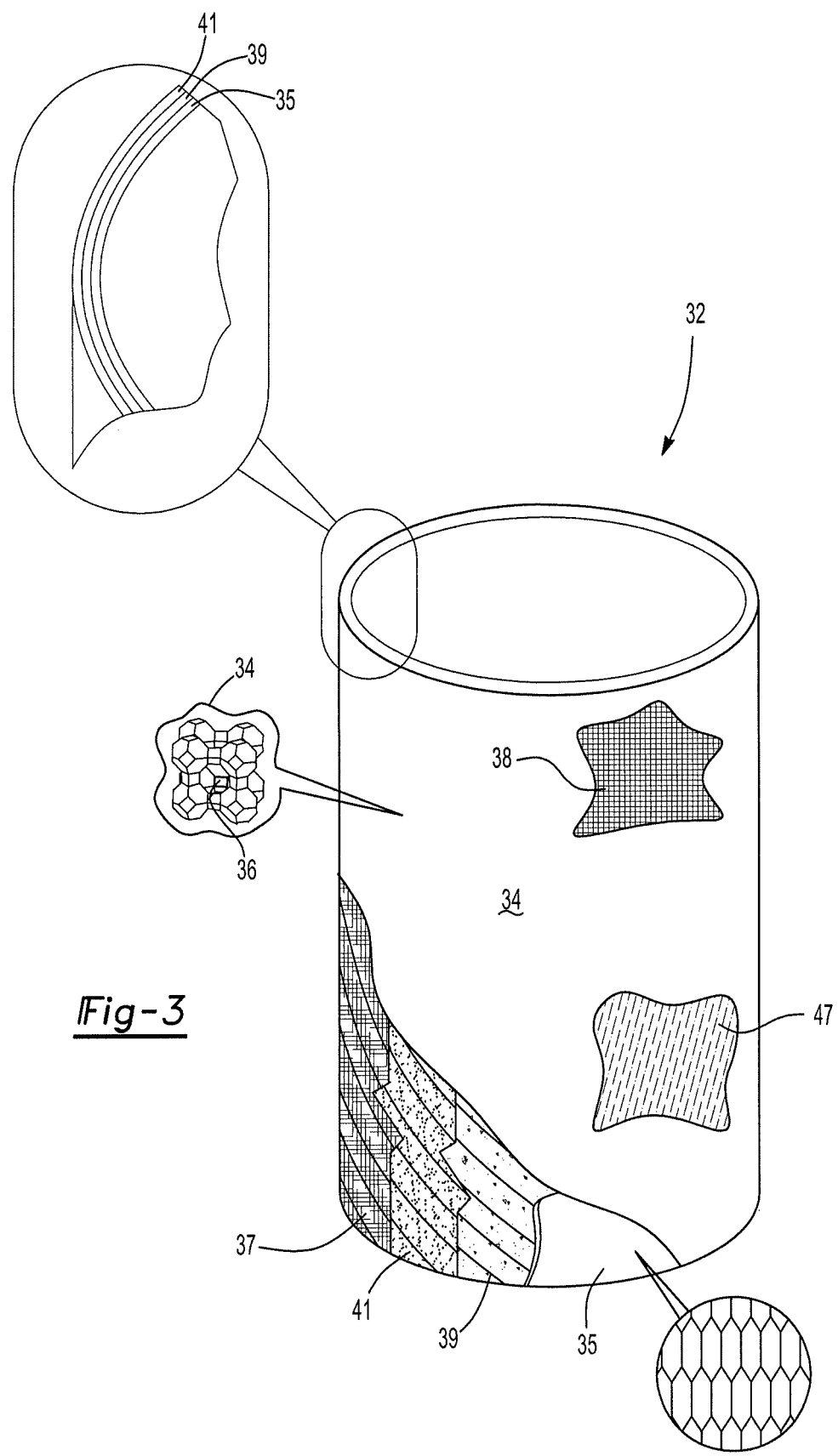
FIG. 3 shows a partial cut out perspective view of the filter membrane of the present invention including alternative embodiments.

In another embodiment, and as best seen in FIG. 3, the carrier membrane 38 may also be cladded with a graphene membrane 39, shown as oxidized or reduced octagonal sheets or strips of carbon. This is often illustrated as a microporous substrate roll or ribbon 37, e.g., copper foil 35 (bottom, dark layer), upon which to vapor deposit graphene 39 (middle layer) and coated with a porous plastic 41 (top layer). In another similar format, the tri-layer tape or ribbon 37 includes two ribbons overlying a carrier cylinder, as the carrier filter 26 equivalent. Massachusetts Institute of Technology has recently perfected means to commercially generate ribbons or rolls of this nano-porous graphene. That octahedral graphene structure, as illustrated at 37 of FIG. 3, is thus commercially available using furnaces and such devices, described as bundled in a tri-sheet roll, as represented in FIG. 3 at in 37 and 39. The ribbon 37 may also be laid over an outer surface of the inner annular filter element 26 to form and define the filter membrane 32. Therefore, the filter membrane 32 may be adhered to the inner annular filter element 26 while still being disposed between the first annular filter element 26 and the second annular filter element 24. In this embodiment, the fabrication copper foil support 35 would be removed and the filter membrane 32 is defined by either the porous plastic 41 or the zeolite/graphene hybrid 39 or both, depending on molecular sieve requirements. This arrangement provides unique mechanical support to the membrane 32. Further, this arrangement provides differential and sequential separation of solubles from fluids when molecular size and weight vary. It should be understood that the membrane 32 porosities may be synthesized with different affinities and porosities, thus providing multicomponent separation.

By comparison, the zeolite 34 provides synthetic porosities, generally on the order of 0.5 nanometers, which, as a slurry, can be 3D printed and laser fused in a single sheet or single thin film sheet on the surface of the carrier membrane 38. In addition to zeolite 34 and graphene 39, there are other hybrid combinations, where zeolite 3D laser printing may be needed to bind together ribbons or sheets of graphene to form larger surface areas, depending on the filtrate throughput required. Zeolite and graphene can be selected for comparable porosities and surface chemistries. Both zeolite and graphene media transport similarly through microchannels-networking between surface porosities. Other membrane-filter media are within the scope of this invention including acrylamide, organometallic molecular sieve agents, equivalents, and combinations as may be or become available. The space interior to the two annular filters 28 and 30 may not only include membranes formed from zeolite 34 and graphene 39 and the like, but also be packed with, for example, bone char. One contemplated compound is polycalcium phosphate, which has a strong affinity for a recently recognized toxins, polyfluoroalkyl chemicals, where the affinity constants are reportedly in the $10^{-32}$ range, as in lower parts per trillion. In order to sequester trace quantities of unwanted elements to comply with federal safety standards, a layered combination of the nano-porous membranes described above and agents, such as hydroxyapatite, could be used to isolate quantities of unwanted constituents for analysis and remediation. Transport rate of filtrate, in this embodiment oily constituents, across the filter membrane 32 is believed to be inversely proportional to membrane thicknesses and porosity of the graphene, zeolite and adsorbent constituents. Spray or dipping application of zeolite 34 slurry onto the carrier membrane 38 will form a film having an estimated 5 nanometers in thickness, preferably 0.5 as a monolayer. The 5 nanometer thickness is sufficient for desirable filtration rates, being orders of magnitude better than reverse osmosis membranes. As set forth above, desirable porosity ranges for the zeolite 34 and/or graphene 40 should be between about 0.3 and 0.5 for optimal throughput.

It should also be understood that that the membrane 32, and more specifically the aperture 36 disposed in the graphene as illustrated provides the ability to tailor, for example, the size of the membrane apertures 36 in the synthetic process to suit the molecular size selection requirements. Further, both the zeolite and graphene porosities may be selectively modified to generate reactive ionized surfaces, enabling enhanced affinity for or exclusion of the constituent being selected for extracted from the plant matrix.

In order to maintain membrane integrity under pressure and at optimal thickness, it is desirable that both inner and outer annular filter elements 26, 24 leave as little spacing as possible to tightly contain the membrane 32 or bulk adsorbents 34, 39, 42 to withstand rigorous filtration pressures. Depending upon the concentration of the oily constituent, the viscosity of the filtrate could be quite high. It is understood that the filter membrane 32 is also supported by its location between the outer annular filter element 24 and the inner annular filter element 26. While the Figures show radial or concentric space between the outer annular filter element 24, the filter membrane 32 and the inner annular filter element 26, the radial spacing is only on an order of microns enabling the annular filter elements 24, 26 to properly support the filter membrane 32 during both water filtration and cleaning cycles by way of backwashing. During assembly, the outer annular filter element 24 is twisted counter clockwise, or in reverse of the direction of the outer annular coil 28 to increase the inner diameter of the outer annular filter element 24 by several microns. The increased inner diameter of the outer annular filter element 24 provides the space to insert both the filter membrane 32 and the second annular filter element 26, disposed internally of the first filter element 24. After insertion, the reverse twist of the outer annular coil 28 is released providing a singular ionic reactor element formed from the outer annular filter element 24, the filter membrane 32 and the second annular filter element 26.

By way of operational example, a filter membrane 32 having a radius of about five inches and an axial length of about 36 inches provides a throughput increase of about twenty five fold over a multilayer membrane of the type used in a reverse osmosis system. Such filtration enhancements may be achieved by applying thin films to one or both of the filter elements 24, 26. As such, filtration enhancements are achieved by applying thin films to the annular coils 28, 30 as will be explained further herein below. It will be further understood that thin film applications, either graphene and/or zeolite films, when applied first to internal annular filter element 26 then clamped in situ by the outer annular filter element 24 as described, constitute an integrated unit. Unlike the continuous rollout processes presently available, requiring copper foil support and mesoporous polyacrylamide covering, to contain the graphene/zeolite film, the integrated unit described herein has the film deposited directly upon an outer surface of the inner annular filter element 26 and contained between and the outer annular filter element 24. This unit, as represented, enables filtration from outside in and backwash from inside out. Further, the thin graphene and/or zeolite film is structurally stabilized between filter elements 24, 26, preventing it from folding upon itself and preventing its porosities from swelling or shrinking due to solvent interaction or applied pressures. The reverse twist assembly of the outer annular coil 24 provides a singular ionic reactor element formed from the outer annular filter element 24, the filter membrane 32 and the inner annular filter element 26.

Zeolites slurries with binding agents have been developed to form the filtration membrane 38. As noted above, such slurries may also be used to provide a thin coating to the inner side of the inner annular filter element 26, with multilayered thicknesses between 5 and 10 nanometers, but preferably 0.5 nanometers as monomolecular film. The inner annular filter element 26, protects the filter membrane 32 from being blocked by sediment and is self-cleaning by way of backwash to clear filter membrane 32 of any accumulated sediment or plant residuum, and provides the means to ensure continuous operation. Desalinating zeolite membrane structures was anticipated recently by Sayed H. Jamali, et al., j. Physical Chemistry, 2017 and Z. In Cao, et al., Science Advances, 2018, in this publication describes nano-sheets prepared by a dip method on macro-porous alumina substrate, with a laminated thickness of from 100 to 500 nanometers, where the permeability to water and salt rejection varies inversely with thickness, and pressure difference across the membrane. It is believed this process may also be used to prepare nano-sheets useful in the constituent extraction from plants as described herein. The optimal thickness and support structures described herein are made possible by the unique properties of the spiral filtration elements 24, 26. These elements 24, 26, together with other adsorptive and/or laser etched spiral annular components, provide options as may be needed for management of plant extracts.

The invention of the present application also contemplates, directly coating the inner annular filter element 24 directly with graphene, rather than first coating a copper substrate. In this embodiment, the filter membrane 32 is formed onto an outer surface of the inner annular filter element 24 in, for example, a seed furnace. If desired, the porous plastic 41, in one embodiment acrylamide, is formed over the graphene layer disposed upon the inner annular filter element 24. However, either embodiment is provide structural integrity, even when exposed to high pressures, because the membrane 32 is sandwiched between the inner outer filter element 24 and the outer annular filter element 24, together locking the membrane 32 in place.

Figure 4:
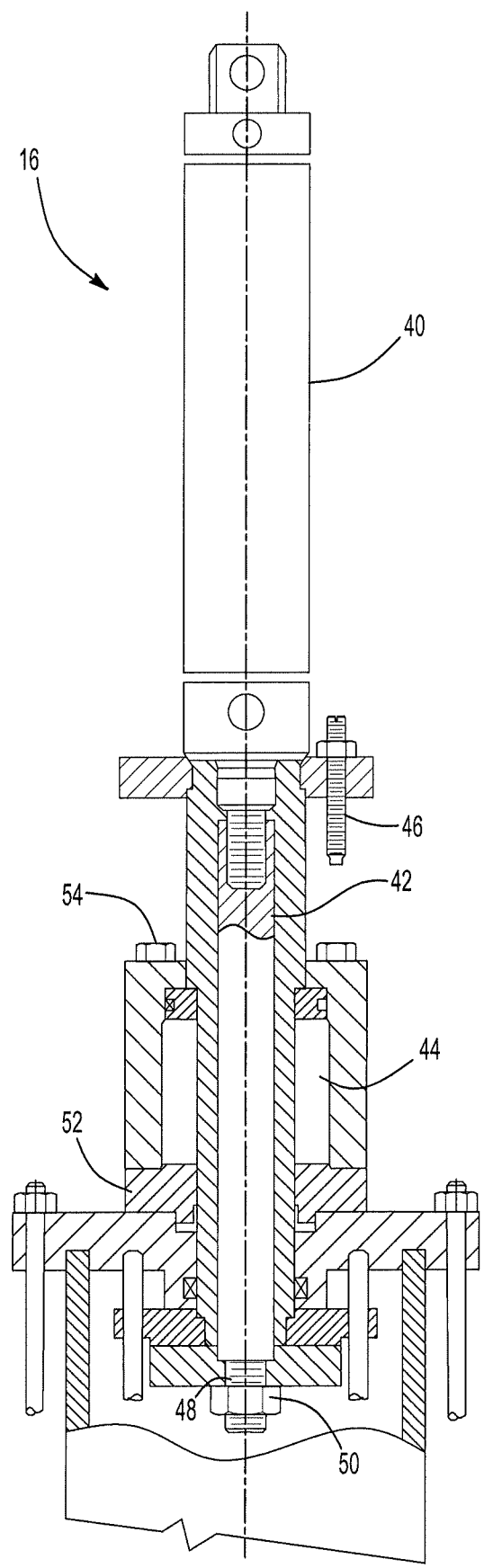
FIG. 4 shows a side view of a drive mechanism used for adjusting porosity of inner and outer annular filter elements.

As set forth above, the outer annular filter element 24 and the inner annular filter element 26 provides variable porosity by way of the aperture drive mechanism 16 best seen in FIGS. 1 and 4. The drive mechanism 16 includes a motor 40 for providing torque to an aperture drive shaft 42. In one embodiment the motor 40 is pneumatic, multi-vane or air driven by pressurized fluid or air. In another embodiment, the motor 40 is an electrically driven servomotor. With respect to the pneumatically driven motor 40, a high gear reduction on the order of 44:1 provides optimal toque. A thru-hole cylinder 44 interacts with adjustable stops 46 to provide microfiltration levels to the outer annular coil 28 and the inner annular coil 30 of about 20 microns during a filtering stage and about 100 microns during a backwash stage. In one embodiment an acme screw 48 extends at the end of the annular drive shaft 42 and receives a piston 50, which is retained by an acme nut 50, or equivalent. The motor 40 actuates the piston 50 for translating adjustment of the porosity of the annular coils 28, 30. In addition, the thru-hole cylinder 44 provides a drive shaft seal 52 and a quick release screw 54 for easily removing the aperture drive mechanism 16 from the housing 12.

Referring again to FIG. 1, the control assembly 20 is located at the second end 22 of the housing 12. A drive element 54 provides rotary movement to a first drive gear 56. The drive element 54 is either a servomotor, a pneumatic motor, or equivalents capable of providing rotary movement to the first drive gear 56. The first drive gear 56 transfers rotary movement to a second drive gear 58. The second drive gear 58 in turn provides rotation to the annular drive shaft 42. A delivery pump 60 delivers ground or fluidize plant material to the annular drive shaft 42 that is received through by way of a plant material inlet 62. The extraction fluid, in this embodiment, a solvent mixture as described above, is injected into the plant material through extraction fluid inlet 63. The plant material/extraction fluid blend exits the annular drive shaft 42 through shaft apertures 43. The delivery pump 60, in one embodiment is a two way pump capable of providing backpressure on the annular drive shaft 42 by reversing pumping direction. Further, pressurized air, heated dry air, or other auxiliary chemicals and agents, including waters, steam and solubilizing compositions may be delivered through the annular drive shaft to the inner housing chamber 13 by way of shaft apertures 43. However, in an alternative embodiment, the plant material and/or extraction fluid may also be pumped directly into the inner housing chamber 13 by the delivery pump 60, and not through the annular drive shaft 42. Alternative delivery pump configurations are within the scope of this invention including a combination of two pumps and cooperative valves used to reverse the flow of the plant material from the housing 12. The control assembly 20 also includes a plant residuum extractor 64 for removing plan residuum from the housing 12 under pressure. A gate valve 65 provides optional selective extraction of the plant residuum through the plant residuum extractor 64 on predetermined intervals so that the optimal reaction time for the extraction fluid may be achieved to develop desired constituent prior to filtering the constituent from through the filter element(s) 24, 26. Referring again to FIG. 1, the plant residuum 64 may take the form of a piston 67 driven by a servo or pneumatic motor 69. It should be understood that the plant residuum may include a high viscosity and the type of extractor 64 is selected to correspond to the level of viscosity anticipated of the plant residuum. Sequential reaction assemblies 10 may result in a plurality of different viscosities at different stages as explained further herein below.

Therefore, the plant residuum is likely highly viscous requiring a high amount of extraction pressure. Therefore, the plant residuum extractor 64, in one embodiment is a pump that works in combination with a conveyor 66 that includes helical fins 68 that are affixed to the annular drive shaft 42. The helical fins 68 are provided rotary movement from the drive element 54 for conveying plant residuum toward the extractor 64. In one exemplary embodiment, the conveyor 66 includes a travel radius of about three inches and having a length of about 36 inches. A conveyor 66 having these dimensions would be run at a rate of about 30 rotations per minute depending upon reaction requirements and viscosity of plant residuum. However, it should be understood that solvent remaining with the residuum may also reduce viscosity of the residuum lessening the pumping demands of the conveyor 66 and the extractor 64. The helical fins 68 include a generally uniform diameter, which is believed to prevent accumulation of residuum or other organic byproducts from concentrating irregularly upon the filter membrane 32. Rapid consistent movement of the oily constituent that passes through the first annular filter element 26 over the membranes 32 internal surface provided by the conveyor 66 fins 68 is thus achieved. However, in some applications it is desirable that the helical fines 68 are not of uniform diameter, but are frustoconical or angled at about 10 degrees, decreasing in diameter in a direction toward the second end 22 of the assembly 10. This is best represented in FIG. 7 in which the fins 68 include a wider diameter at the first end 18 of the assembly 10 than at the second end 22 of the assembly. It is believed this shape provides benefits to moving the increasingly viscous residuum to the dried waste extractor.

As set forth above, the extraction material is delivered into the assembly at an elevated temperature, even at superheated temperatures causing the constituents to approach a vapor stage, or at least to a temperature believed to extract a desired constituent. It is desirable to rapidly cool the constituents after passing through the filter elements 26, 24. Therefore, the filtrate side 27 of the assembly 10 includes a cooling element 29. In this embodiment, the cooling element 29 takes the form of a continuous cooling line that circumscribes the outer filter element 24 extending between the first end 18 and the second end 22 of the housing 12. In one embodiment, the cooling element 24 is disposed in the filtrate chamber 27. Alternatively, the cooling element is disposed exterior to the housing 70 and cools the constituent by absorbing heat energy through the housing 70 wall. It should be understood that cooling fluid, such as, for example Freon circulates through the cooling element 24 in a known manner. It should further be understood that the cooling element may take other configurations, so long as the enough heat energy is extracted from the filtrate to condense and/or liquefy the vaporized product at a temperature slightly less that of the vaporizing product being extracted. The so extracted filtrate is physically characterized by both vaporization and condensation temperature. Thus, it is desirable that the cooling element provide enough heat reduction to the filtrate chamber 27 to maintain the filtrate, i.e. extraction fluid and constituent mix just below the vapor temperature of the constituent. Maintaining the temperature below the vapor temperature provides a double means for establishing purity of the constituent through passing the constituent through its vapor point, from vapor to liquid phase, and the condensation of the constituent.

Referring now to FIG. 4, the continuous process by which the constituent is separated from the plant material will now be explained by way of a schematic representation. It should be understood that the process described herein is merely exemplary. The details associated with the extraction are for ease of understanding to one of ordinary skill in the art.

The helical fins 68 that are attached to the annular drive shaft 42 convey centrifugal force to the plant material disposed in the inner housing chamber 13 when the annular drive shaft pivots around axis a forcing the separated constituent disposed in the plant material radially outwardly of the housing 12. Should the annular drive be frustoconical in shape as described above, there will be a centrifugal force also conveyed parallel to the drive, from entrance to exit end, to facilitate direction of flow within the cylinder 70. Further, turbulent movement of the plant material generated by rotation of the helical fins 68 prevents the filter membrane 32 from being blocked by sediments or adhesive byproducts, precipitating plant material or viscous supersaturated plant material, thus providing for continuous operation of the assembly 10, other than during self-cleaning backwash cycles. During the introduction of plant material and extraction fluids to the assembly 10, and while the annular drive shaft 42 is providing centrifugal force to the plant material disposed in the inner housing chamber 13, the aperture drive mechanism 16 causes the piston 50 to compress the first and second annular filter elements 24, 26 thereby reducing the spacing between adjacent coils of the outer annular coil 28 and the inner annular coil 26 respectively. Reduced spacing provides filtration apertures of about 20 microns or less for filtering larger residuum while allowing the constituent to pass through the second annular filter element 26, which is disposed radially inwardly of both the filter membrane 32 and the outer annular filter element 24.

It should be understood that plant material disposed in the inner chamber 13 is rapidly rotated by the spinning helical or screw conveyor fins 68 to drive the constituent filtrate radially outwardly through the outer annular filter element 24, and when included, through the inner annular filter element 26 and the filter membrane 32. After passing through the outer annular filter element 24, the constituent enters the filtrate chamber 27 where it is condensed and/or cooled and exits through the outlet 72. In one embodiment, the variable filter apparatus 24 is disposed at a slight angle of about 10° to allow drainage through the outlet 72 so long as the constituent is not excessively viscous after cooling. Alternatively, negative pressure or vacuum pressure is applied to the outlet 72 draw out the constituent when the constituent is anticipated to exceed a threshold viscosity. The extraction fluid inlet 63 includes a three way valve 61 that provides the ability to inject heated steam, and the like to the plant material inlet 62 with the ratios being modified to meet specific reaction and extraction rates. An optional hopper (not shown) is used to deliver plant material to the plant material delivery pump 60.

In one embodiment, the extraction fluid is immediately introduced to the inwardly bound plant product at elevated temperature to initiate the reaction between the extraction fluid and the plant material to allow accelerate extraction of the constituent prior to turbulent mixing in the inner housing chamber 13 by the conveyor 66. The velocity of these fluids entering into the porous shaft 42 is adjustable to obtain target reaction rates. Knowing the density of the plant material, wetness, pacific heat, etc. beforehand along with a determination of the whether the temperature will be raised to above the boiling point will provide the ability to calculate the desired reaction time and cost. As explained further below, a plurality of assemblies 10 may be connected in series or in parallel having different operating parameters for extracting different and desirable constituents from the same or combinations of different plant products.

After passing through the inner annular filter element 26 through the centrifugal force generated by the spinning helical fins 68, the separated constituents passes through the inner annular filter element 26 and contact the filter membrane 32 that is concentrically disposed between the outer annular filter element 24 and the second annular filter element 26. Porosity of the filter membrane is adjustable to accommodate different constituent extraction needs. However, plant matter and other reaction byproduct having a diameter greater than about 20 microns dos not reach the filter membrane 32 due to being entrapped by the inner filter element 26. As explained in detail above, the zeolite 34 or graphene 39 or graphene-zeolite hybrid 41 or adsorbent 47 (FIG. 3) upon being applied as thin film, shown as zeolite (or alternate media noted) membrane 32 (FIG. 3) provides filtration providing porosities, optimally less than about 0.5 nanometers, which is capable of capturing microscopic plant material and objectionable byproduct disposed in the plant material while allowing only high quality constituent to pass into the filtrate chamber 27. The particulate plant material collects on the inner surface of the zeolite (or other such media noted) membrane 32 allowing the oily constituent, being at, or near its vapor stage, to pass through the membrane 32 radially outwardly through the outer annular filter element 24 into the clean filtrate chamber 27. The membrane 32 may also include adsorbent media having an affinity for dissolved plant material or other constituent not yet ready for extraction from the plant material. Such dissolved plant materials are eluted (desorbed) from the media, for further processing in a second assembly as will be explained further herein below.

Figure 5:
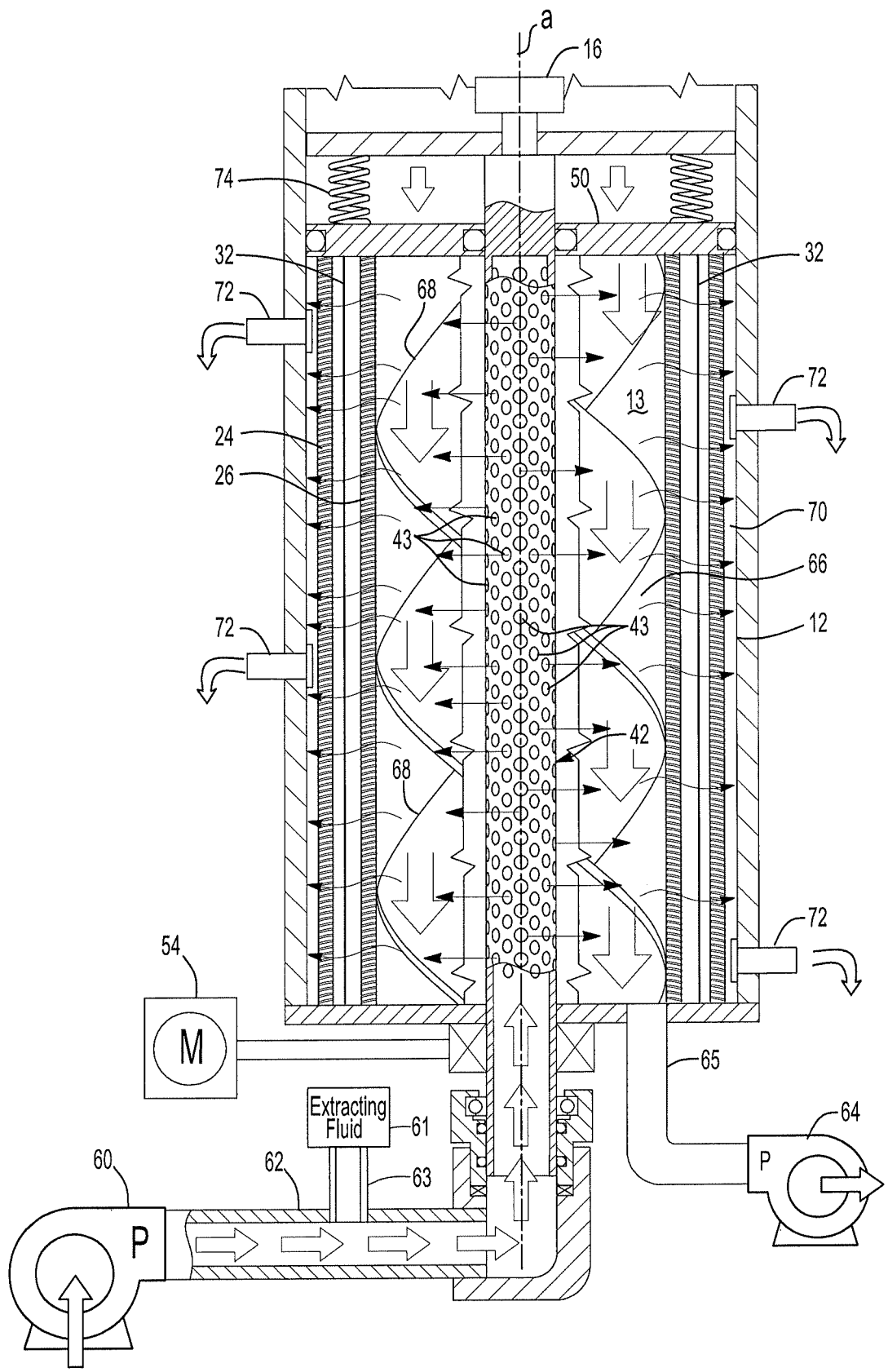
FIG. 5 shows a schematic view of the assembly of the present invention with constituent and extraction fluid flow direction.
Figure 6:
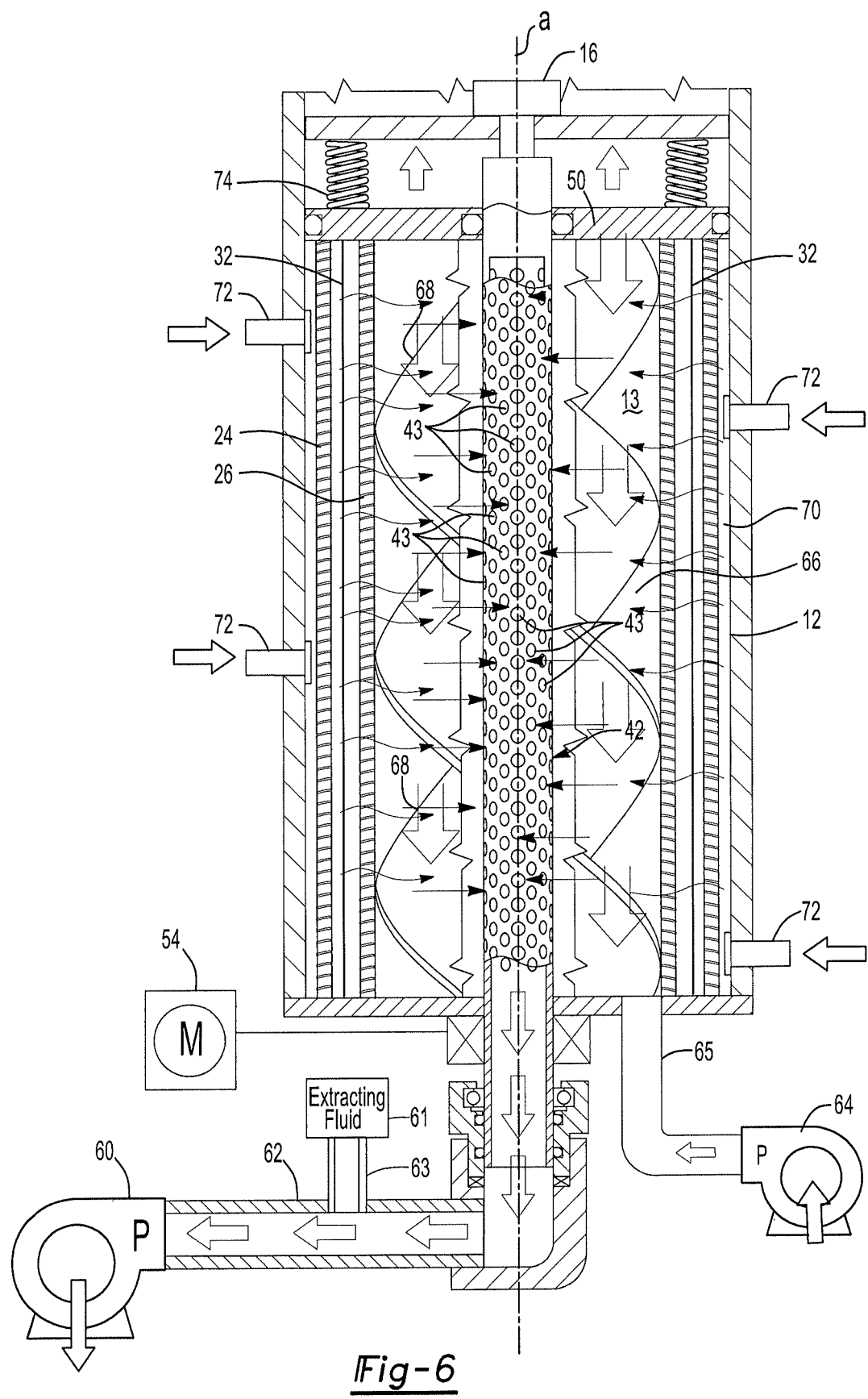
FIG. 6 shows a schematic view of the assembly representing backflush flow direction.

Oily, and now condensed, constituent is removed from the filtrate chamber 27 through filtrate outlet 72. In the present example, desirable plant constituent extracted through the water outlet 72 that is still includes useful products or constituents is available for further processing once removed from the inner housing chamber 13. When necessary, a vacuum or negative pressure is created by way of a pump (not shown) to draw the constituent out of the filtrate chamber 27 though the filtrate outlet 72. It is contemplated by the inventor that vacuum or negative pressure of about 0.014 psi will suffice. FIGS. 5 and 6 shows multiple filtrate outlets 72 spaced along the housing 12. However, it should be understood that a single outlet 72 may also suffice for the purpose of extracting the constituent.

A desirable external pressure at the plant material inlet 62, ranges between about 120 psi to about 150 psi. A desirable temperature at this pressure range is preferably about 120° F. However, optimal pressure and temperature is determined based upon the physical and chemical characteristics of the target constituent being extracted and the type of plant material being introduced to the assembly 10. Additional byproducts contained in the plant material may be removed separately by automatic backwashing, as directed by a controller, such backwash will remove buildup of these byproducts from the inner annular filter element 26 providing the ability for continuous processing of plant material. As set forth above, some of these byproducts may include desirable characteristics and are available for extraction in later processing.

During extended operation, plant material begins to collect in the inner housing chamber 13 and can substantially increase the weight percent and viscosity of the plant material in the mixture or residuum disposed in the inner housing chamber 13. Therefore, the conveyor 66, while also creating centrifugal force to drive the mixture radially outwardly and longitudinally, conveys the residuum downwardly in the inner housing chamber where the residuum is removed from the inner housing chamber 13 though the plant material extractor 64 by way of the outlet 65. At this location, the residuum is believed to include a higher viscosity due to the high concentration of the filtered plant material in the residuum. Should the viscosity exceed a level that disadvantages extraction of the plant material from the inner housing chamber 13, the extraction pump 64 provides negative pressure to the plant material outlet 65, thereby facilitating removal of the filtered plant material and residuum.

As set forth above, the plant material collects on an inner surface of the filter membrane 32. When fluid pressure on the membrane 32 exceeds a predetermined limit, or at scheduled cycle times during extended operation, a controller, that is integrated with the assembly, initiates a backflush operation to reverse the flow of filtrate through the outer annular filter element 24, the filter membrane 32, and subsequently through the inner annular filter element 26 to remove buildup of organic matter, on, at least, the filter membrane 32 and the second annular filter element 26. The reverse flow process of the backflush operation is represented in FIG. 6.

During the backflush operations, the plant material delivery pump 60 reverses direction to draw the delivered plant material and retained residuum from the inner housing chamber 13. In addition, pressure is released on the outer annular filter element 24 and the inner annular filter element 26 to increase porosity from about 20 microns used for filtration to about 100 microns used for the backflush operation. A biasing element 74 maintains a desirable biasing force on the outer annular filter element 24 and the inner annular filter element 26 to maintain porosity in the 100 micron range during backflush operations. The piston 50 compresses the biasing element 74 during filtration and release the compression of the biasing element 74 while the assembly 10 is being backwashed. In addition, negative pressure is no longer maintained on the water outlet 72 during backflush operations so that the water may flow freely in the reverse direction through the filter membrane 32 by an amount believed to remove a buildup of materials on the filter membrane 32 and other larger contaminants entrapped by the second annular filter element 26.

Relevant to the invention of the present application is the maintenance of temperature at each heat exchanger associated with each cooling element 29 serving their respective reactor cylinders when arranged in series as explained herein below. For example, the terpenes of cannabis have boiling points in excess of 350° F., THC and THCa boil at 314° F. and 220° F., respectively; CBD boils at 248° F., while CBN and CBC do so at 365° F. and 420° F., respectively. Therefore, the ability to maintain temperature near these values provides the ability to separately extract different of these constituents.

Figure 8:
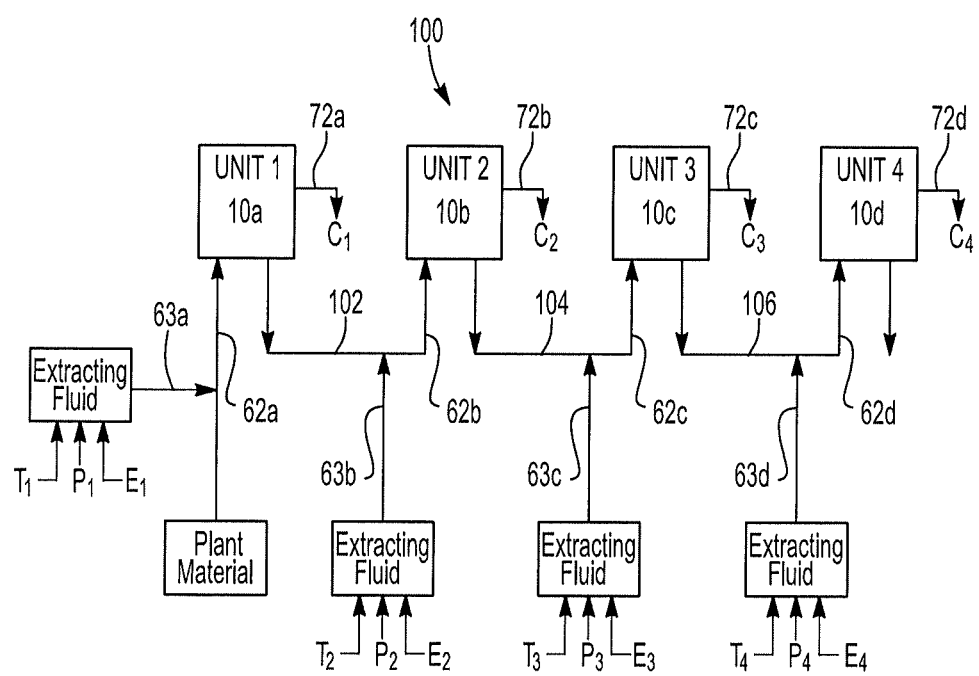
FIG. 8 shows a plurality of reactor assemblies aligned in series for seriatim removal of constituents.

As alluded to above, the assembly 10 may be arranged in series to provide additional extraction of alternative or different plant constituents at different or higher differential pressures and temperatures. This is best represented in FIG. 8 where an extraction system is generally shown 100 and a plurality of reaction assemblies 10a, 10b, 10c and 10d are shown arranged in series. Each assembly 10a, 10b, 10c, 10d perform in a manner similar as is explained herein above and like elements are disclosed with like element numbers with sequential alphabetical suffixes. The serial arrangement of the assemblies 10a, 10b, 10c, 10d provides the ability for continuous extraction of different and useful constituents from any plant material, each exhibiting different extraction properties requiring different processing temperature, pressure and extraction fluids.

The first assembly 10a operates much as explained above. The extracting fluids are injected into the extraction fluid inlet 63a for mixing with the plant material either in the plant material inlet 62a or upon entry into the inner housing chamber 13a. The temperature T1, pressure P1 and extracting fluid content E1 are selected for the purpose of extracting a first constituent C1. After reaction in the inner housing chamber 13a and filtering into the filtrate chamber 27a, the first constituent C1 is evacuated though constituent outlet 72a and subject to further processing separate from this system, if necessary. The first residuum R1 is evacuated from the inner housing chamber 13 and transferred into to the second assembly 10b via transfer 102.

At the second assembly 10b second extracting fluids are injected into the second extraction fluid inlet 63b for mixing with the plant material either in the second plant material inlet 62b or upon entry into the second inner housing chamber 13b. The temperature T2, pressure P2 and extracting fluid content E2 are selected for the purpose of extracting a second constituent C2 not extracted in the first assembly 10a. In like manner as with the first assembly 10a, the second constituent C2 exits the second assembly 10b though a second constituent outlet 72b. The second residuum R2 is then evacuated from the second inner housing chamber 13 and transferred into to a third assembly 10c via a second transfer 104.

As set forth above, the annular drive shaft 42 serves as a conduit to deliver both plant materials and extraction fluids to the inner housing chamber 13 via apertures 43. It may be desirable to locate a one way check valve in the transfer lines 102, 104, 106 that deliver the plant material/extraction fluid and residuum to the annular drive shaft of the following assembly 10b, 10c, 10d to prevent unwanted backflow. A temperature controlled alcohol-water mixture delivery unit, as available through Micropyretics of Cleveland, Ohio is included to provide desired thermal properties to the extraction fluid. Thus, the extraction fluid may be delivered to a T pipe fitting internal to the annular shaft 42. Each shaft 42 may be 36 inches in length and 12 inches in diameter with the screw conveyor 66 running at 30 rpm maximum or of lesser dimensions and velocity, if it should be determined that extraction is incomplete at a throughput of 7 pounds per minute.

The process may be repeated to as many sequential assemblies as there are constituents desirable to extract from plat matter that require differing process parameters. For example, third and fourth assemblies 10c, 10d may be added in series to extract third and fourth constituents C3, C4. As such, a third extracting fluid E3 having third temperature T3, third pressure P3 is injected at third plant material inlet 62c with third residuum being evacuated from the third inner housing chamber 13 into a fourth assembly 10d via a third transfer 106. Finally, remaining residuum may optionally be extracted from the fourth assembly 10d as waste product.

In a publication, "Industrial Scale Natural Products Extraction", 2011, page 5, there is reference to vacuum distillation or hydro-distillation, and condensation of oil and water distillate; but not in highly efficient, continuously operating, serial assemblies as represented in FIG. 8. Separate delivery of the extraction fluid through T coupling or the like just distal to the check valve enables the steam/solvent mixture to be injected into the second reactor assembly 10b and following assemblies at a temperature higher than the temperature of the prior assembly 10a and higher than the temperature of the residuum disposed in transfer line 102. This is also true of sequential assemblies 10c, 10d. The sequence length will depend on the number of desired chemical components extractable and on solid's constituent solubility and vapor pressure.

As noted in the above embodiment, each cooling element 29 is set by external controls to condense the alcohol-water mixture's temperature as shown circulating to just below the dew point for the alcohol or other solvent. Since the alcohol or similar solvents are used as solvents, soluble in both water and the plant's product, upon extracting that product at a temperature above which that product vaporizes. The vaporized mixture is desirably condensed separately, the water first due to the assembly 10a, 10b, 10c, 10d reaction extraction temperature, then the alcohol containing the valuable product. The solvent-product combination is thus essentially free of water, but containing the volatile solvent. Both the solvent product, in this example in ethanol, may or may not require separation. Both the condensed waster at 212° F. and alcohol at 78° F. exit the assembly through filtrate exit 72, where condensation temperatures are set by the refrigerant source controls and cooling element 29. The extraction temperature of the first inner reaction chamber 13 in the first assembly 10a may be 220° F. to solubilize THC and 248° F. in the second assembly 10b to remove CBD at 248° F. and so on until all of the desired constituents are extracted from the plant material. The extracted products and water will be similarly condensed and collected as explained above. Should the solvent, ethanol in this embodiment, itself need removal, there may be a split at the delivery point with a vacuum condenser, one operating at 78° F. and another at 212° F. for end point product purity purposes, where the industrial suppliers may require pure oil product or in solvent noted.

The invention has been described is in an illustrative manner; many modifications and variations of the present invention are possible, including removal of toxins from fluids, in light of the above teachings. It is therefore to be understood that within the specification, the reference numerals are merely for convenience, and are not to be in any way limiting, and that the invention may be practiced otherwise than is specifically described. Therefore, the invention can be practiced otherwise than is specifically described within the scope of the stated claims following this first disclosed embodiment.

What is claimed is:

1. A method of extracting constituents from cannabis plant material, comprising the steps of:
   providing a first and a second reactor assembly, each assembly including a first annular filter element defined by an annular coil of a flat wire providing adjustable filtration apertures to said first annular filter element defining a reaction chamber being disposed radially inwardly of said first annular filter element and a filtrate chamber being disposed radially outwardly of said first annular filter element;
   delivering a stream of cannabis plant solids including a first constituent and a second constituent into said reaction side of said first reactor assembly;
   injecting first extracting fluids being disposed at a first temperature and composition into said reaction side of said first reactor assembly for solubilizing the first constituent of the cannabis plant solids and separating said first constituent from the cannabis plant solids through said first annular filter element into said filtrate chamber of said first reactor assembly;
   transferring residuum disposed in said reaction chamber of said first reactor assembly to said reaction chamber of said second reactor assembly; and
   injecting second extracting fluids into a reaction chamber of said second reactor assembly with the residuum, said second extracting fluids being disposed at a second temperature and composition for solubilizing the second constituent of the cannabis plant solids and separating the second constituent through said first annular filter element of said second reactor assembly into said filtrate chamber of said second reactor assembly.

2. The method set forth in claim 1, wherein said step of injecting first extracting fluids being disposed at a first temperature and composition into said reaction chamber of said first reactor assembly is further defined by injecting fluids being disposed above a vapor temperature of the first constituent thereby vaporizing the first constituent.

3. The method set forth in claim 2, wherein said step of injecting second extracting fluids being disposed at a second temperature and composition into said reaction chamber of said second reactor assembly is further defined by injecting fluids being disposed above a vapor temperature of the second constituent thereby vaporizing the second constituent.

4. The method set forth in claim 1, wherein said step of injecting first extracting fluids is further defined by providing a solvent and water mixture suitable for solubilizing said first constituent.

5. The method set forth in claim 1, wherein step of injecting second extracting fluids is further defined by providing a solvent and water mixture suitable for solubilizing said second constituent.

6. The method set forth in claim 1, further including a step of cooling the first constituent disposed in said filtrate chamber of said first reactor assembly to a temperature below the vaporization temperature of the first constituent thereby condensing the first constituent.

7. The method set forth in claim 1, further including a step of cooling the second constituent disposed in said filtrate chamber of said second reactor assembly to a temperature below the vaporization temperature of the second constituent thereby condensing the second constituent.

8. The method set forth in claim 1, further including a step of reversing a flow of the first constituent though the first annular filter element of the first annular reaction assembly thereby cleaning the first annular filter element of the first annular reaction assembly.

9. The method set forth in claim 1, further including a step of reversing a flow of the second constituent though the first annular filter element of the second annular reaction assembly thereby cleaning the first annular filter element of the second annular reaction assembly.

10. The method set forth in claim 1, further including a step of providing a second annular filter element defined by an annular coil of a flat wire providing adjustable filtration apertures of said second annular filter element and said second annular filter element being disposed radially outwardly of said first annular filter element in each of said first reactor assembly and said second reactor assembly.

11. The method set forth in claim 10, further including a step of providing a filter membrane and disposing said filter membrane between said first annular filter element and said second annular filter element.

12. The method set forth in claim 11, further including a step of said filter membrane providing ionic reactivity to the first constituent passing through said filter membrane of said first reaction assembly and said second constituent passing through said filter membrane of said second reaction assembly.

13. The method set forth in claim 1, further including a step of forcing residuum disposed in said reaction chamber of said first reactor assembly toward a residuum exit thereby transferring the residuum from said reaction chamber of said first reactor toward said reaction chamber of said second reactor.

\* \* \* \* \*